United States Patent
Ludin

(10) Patent No.: US 7,334,594 B2
(45) Date of Patent: Feb. 26, 2008

(54) APPARATUS AND METHOD FOR ADJUSTING A LOCKING MECHANISM OF A SHUNT VALVE

(75) Inventor: Lev Ludin, Newton, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 399 days.

(21) Appl. No.: 11/170,795

(22) Filed: Jun. 29, 2005

(65) Prior Publication Data

US 2007/0005000 A1    Jan. 4, 2007

(51) Int. Cl.
*F16K 35/16* (2006.01)
*A61M 27/00* (2006.01)

(52) U.S. Cl. .................. 137/1; 137/524; 137/535; 137/539; 137/383; 137/385; 128/903; 604/8; 604/9; 607/60

(58) Field of Classification Search ............... 137/383, 137/384.6, 385, 524, 530, 535, 539; 604/8, 604/9; 607/60; 128/903
See application file for complete search history.

(56) References Cited

U.S. PATENT DOCUMENTS

| | | | |
|---|---|---|---|
| 3,886,948 A | 6/1975 | Hakim | |
| 4,332,255 A | 6/1982 | Hakim et al. | |
| 4,387,715 A | 6/1983 | Hakim et al. | |
| 4,443,214 A | 4/1984 | Marion | |
| 4,532,932 A * | 8/1985 | Batty, Jr. .................. | 600/302 |
| 4,551,128 A | 11/1985 | Hakim et al. | |
| 4,595,390 A | 6/1986 | Hakim et al. | |
| 4,615,691 A | 10/1986 | Hakim et al. | |
| 4,772,257 A | 9/1988 | Hakim et al. | |
| 5,637,083 A | 6/1997 | Bertrand et al. | |
| 5,643,194 A | 7/1997 | Negre | |
| 5,928,182 A | 7/1999 | Kraus et al. | |
| 6,702,249 B2 | 3/2004 | Ito | |
| 6,840,917 B2 | 1/2005 | Marion | |
| 6,926,691 B2 | 8/2005 | Miethke | |
| 7,066,901 B2 * | 6/2006 | Kuth et al. .................. | 604/9 |
| 2001/0002250 A1 | 5/2001 | Burbank et al. | |

(Continued)

FOREIGN PATENT DOCUMENTS

EP    0 982 048 A    3/2000

OTHER PUBLICATIONS

Search Report for EP 06 25 3362.

*Primary Examiner*—Ramesh Krishnamurthy
(74) *Attorney, Agent, or Firm*—Nutter, McClennen & Fish, LLP

(57) ABSTRACT

A shunt valve assembly includes an electromechanical brake mechanism that locks a position of a pressure setting mechanism within a shunt valve assembly. The electromechanical brake can maintain the position of the pressure setting mechanism in the presence of a relatively strong magnetic field to maintain a set pressure differential within the shunt valve assembly. In certain cases, the shunt valve requires repositioning of the pressure setting mechanism within the shunt valve assembly to adjust a fluid flow rate through the shunt valve assembly. A clinician can activate an external controller to transmit a signal to the shunt valve assembly through magnetically coupled antennas between the controller and the shunt valve. The shunt valve assembly utilizes the signal to activate the braking mechanism and unlock the pressure setting mechanism. The clinician then operates the controller to non-invasively reposition the pressure setting mechanism and adjust the pressure at which the shunt valve opens.

24 Claims, 5 Drawing Sheets

U.S. PATENT DOCUMENTS

| | | |
|---|---|---|
| 2002/0026139 A1 | 2/2002 | Bertrand et al. |
| 2002/0058901 A1 | 5/2002 | Marion |
| 2004/0010219 A1 | 1/2004 | McCusker |
| 2004/0143242 A1 | 7/2004 | Ludin et al. |
| 2006/0074371 A1* | 4/2006 | McCusker et al. ............. 604/9 |
| 2007/0004999 A1* | 1/2007 | Miethke ........................ 604/9 |

* cited by examiner

APPARATUS AND METHOD FOR ADJUSTING A LOCKING MECHANISM OF A SHUNT VALVE

CROSS-REFERENCE TO RELATED APPLICATIONS

Not applicable

STATEMENT REGARDING FEDERALLY SPONSORED RESEARCH

Not applicable

FIELD OF THE INVENTION

The present invention relates generally to medical devices for directing bodily fluids from one region of a patient to another region. More specifically, embodiments of the invention relate to shunt systems having an adjustable shunt valve to control the flow of fluid through the system and, even more specifically, an electromechanical locking mechanism that controls the adjustment of the shunt valve.

BACKGROUND

Hydrocephalus is a neurological condition caused by the abnormal accumulation of cerebrospinal fluid (CSF) within the ventricles, or cavities, of the brain. Hydrocephalus, which can affect infants, children and adults, arises when the normal drainage of CSF in the brain becomes blocked in some way. Such blockage can be caused by a number of factors, including, for example, genetic predisposition, intraventricular or intracranial hemorrhage, infections such as meningitis, or head trauma. Blockage of the flow of CSF consequently creates an imbalance between the rate at which CSF is produced by the ventricular system and the rate at which CSF is absorbed into the bloodstream. This imbalance increases pressure on the brain and causes the brain's ventricles to enlarge. Left untreated, hydrocephalus can result in serious medical conditions, including subdural hematoma, compression of the brain tissue, and impaired blood flow.

Hydrocephalus is most often treated by surgically inserting a shunt system to divert the flow of CSF from the ventricle to another area of the body, such as the right atrium, the peritoneum, or other locations in the body where CSF can be absorbed as part of the circulatory system. Various shunt systems have been developed for the treatment of hydrocephalus. Typically, shunt systems include a ventricular catheter, a shunt valve, and a drainage catheter. At one end of the shunt system, the ventricular catheter can have a first end that is inserted through a hole in the skull of a patient, such that the first end resides within the ventricle of a patient, and a second end of the ventricular catheter that is typically coupled to the inlet portion of the shunt valve. The first end of the ventricular catheter can contain multiple holes or pores to allow CSF to enter the shunt system. At the other end of the shunt system, the drainage catheter has a first end that is attached to the outlet portion of the shunt valve and a second end that is configured to allow CSF to exit the shunt system for reabsorption into the blood stream.

Generally, the shunt valve, which can have a variety of configurations, is effective to regulate the flow rate of fluid through the shunt system. In some shunt valve mechanisms, the fluid flow rate is proportional to the pressure difference at the valve mechanism. These shunt valve mechanisms permit fluid flow only after the fluid pressure has reached a certain threshold level. Thus, when the fluid pressure is slightly greater than the threshold pressure level, the fluid flow rate is relatively low, but as the pressure increases, the fluid flow rate simultaneously increases. Typically, the shunt valve allows fluid to flow normally until the intracranial pressure has been reduced to a level that is less than the threshold pressure of the shunt valve, subject to any hysteresis of the device.

Certain conventional shunt valves allow external adjustment of the threshold pressure level at which fluid flow will commence to avoid invasive surgical procedures. In some shunt systems, the shunt valve contains a magnetized rotor to control the pressure threshold of the valve. Physicians can then use an external adjustment mechanism, such as a magnetic programmer, to adjust the pressure threshold of the shunt valve. However, these magnetized rotors can be unintentionally adjusted in the presence of a strong external magnetic field, such as during an MRI procedure. Unintentional adjustment of the pressure threshold could lead to either the overdrainage or underdrainage of CSF, which can result in dangerous conditions, such as subdural hematoma.

Attempts have been made to provide a locking mechanism that prevents unintentional valve adjustment, even in the presence of a strong external magnetic field, while simultaneously allowing intentional adjustment of the pressure threshold. One such approach has been detailed in U.S. Pat. No. 5,643,194, in which Negre describes a locking means having two opposed micro-magnets mounted on the rotor. In the presence of a bi-directional magnetic field, these micro-magnets move linearly in the rotor, in a substantially radial direction, to activate the locking means. However, the Negre locking means does not eliminate the risk of inadvertent valve adjustment in the presence of a strong external magnetic field.

Another approach has been described in U.S. Pat. No. 5,637,083, in which Bertrand et al. describe a valve that includes means for locking the rotor assembly in a desired position. This locking means uses a pin having a first end adapted to engage a series of detents in an outer peripheral surface of the rotor assembly, thereby preventing the rotor assembly from rotating. The locking means is disengaged by a pin-actuating means having two levers that move the pin from a first, extended position, i.e., within the detent(s) in the outer peripheral surface, to a second, retracted position. The first lever is a pivotable lever having a shaft adapted to engage a second end of the pin, while the second lever is a manually actuated lever that is biased to urge the pin into the first, extended position. This manually actuated lever, however, is located within the valve chamber that is used to pump, or flush, fluid from the shunt valve. Thus, by virtue of its location within the pumping chamber, the manually actuated lever, and consequently the pin-actuating means, can impair or inhibit the function of the pumping chamber.

SUMMARY

Embodiments of the present invention significantly overcome a number of the prior art devices and methods and provide an electromechanical brake mechanism that locks or secures a position of a pressure setting mechanism within a shunt valve assembly. The electromechanical brake can maintain the position of the pressure setting mechanism in the presence of a relatively strong magnetic field, such as produced by a magnetic resonance imaging device, to maintain a set pressure differential within the shunt valve assembly. Additionally, in certain cases, the shunt valve requires repositioning of the pressure setting mechanism within the shunt valve assembly to adjust a fluid flow rate through the shunt valve assembly. A clinician can activate an external controller to non-invasively release the electromagnetic brake mechanism from the pressure setting mechanism. When activated, the external controller transmits a radio frequency signal to the shunt valve assembly through magnetically coupled antennas between the controller and the shunt valve. The shunt valve assembly utilizes the signal to activate the braking mechanism and unlock the pressure setting mechanism. The clinician then operates the controller to non-invasively reposition the pressure setting mechanism and adjust the pressure at which the shunt valve opens.

In one arrangement, a shunt valve assembly includes a housing having an inlet port and an outlet port, the housing being configured to carry a fluid between the inlet port and the outlet port. The shunt valve assembly also includes a valve coupled to the housing and in fluid communication with the inlet port and the outlet port. The valve has a pressure setting mechanism configured to adjust a pressure at which the valve releases fluid from the inlet port to the outlet port. The shunt valve assembly includes an electromechanical brake assembly having a brake member disposed in proximity to the pressure setting mechanism and a signal receiver in electrical communication with the electromechanical brake assembly. The signal receiver receives an activation signal and transmits a positioning signal to the electromechanical brake assembly, in response to receiving the activation signal. The positioning signal positions the brake member in a first position relative to the pressure setting mechanism when the activation signal has a first value and positions the brake member in a second position relative to the pressure setting mechanism when the activation signal has a second value. The electromechanical brake effectively locks the pressure setting mechanism within the housing to limit or prevent movement of the pressure setting mechanism and to maintain a set pressure threshold within the shunt valve assembly when exposed to the magnetic field.

In one arrangement a shunt valve system includes a shunt valve assembly and a controller. The shunt valve assembly includes a housing having an inlet port and an outlet port, the housing configured to carry a fluid between the inlet port and the outlet port, and a valve coupled to the housing, the valve having a pressure setting mechanism configured to adjust a pressure of the fluid carried by the housing. The shunt valve assembly also includes an electromechanical brake assembly having a brake member disposed in proximity to the pressure setting mechanism, and a signal receiver in electrical communication with the electromechanical brake assembly. The controller has a signal transmitter that transmits an activation signal to the signal receiver of the shunt valve assembly. The signal receiver receives the activation signal and transmit a positioning signal to the electromechanical brake assembly, in response to receiving the activation signal. The positioning signal positions the brake member in a first position relative to the pressure setting mechanism when the activation signal has a first value and positions the brake member in a second position relative to the pressure setting mechanism when the activation signal has a second value.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1:
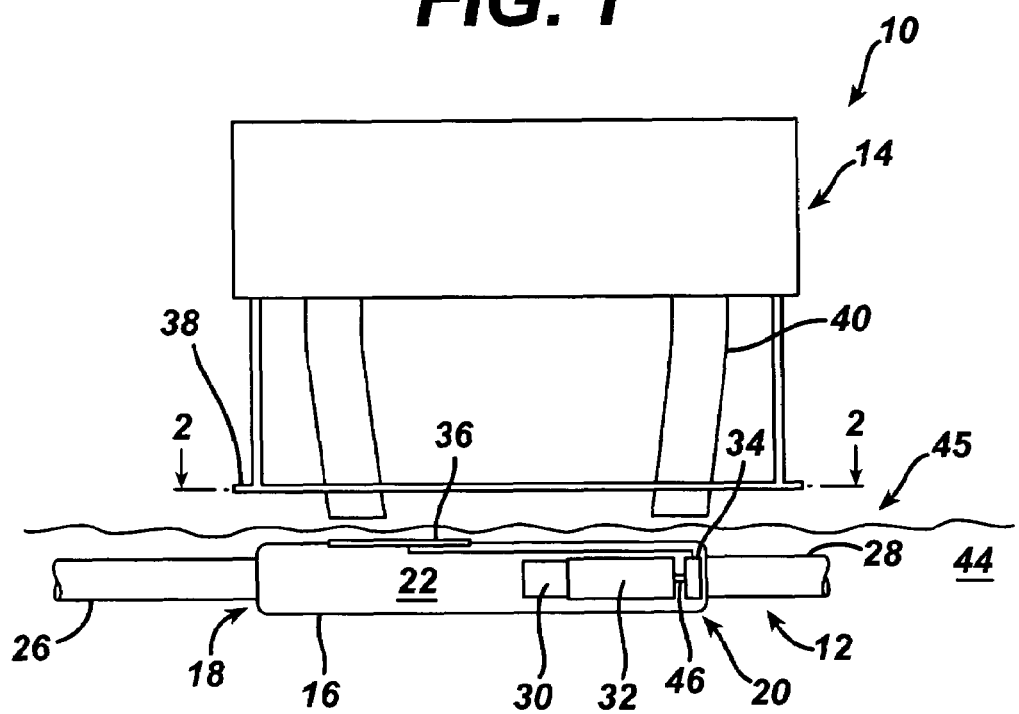
FIG. 1 illustrates a sectional view of a schematic representation of a shunt valve system, according to one embodiment of the invention.
Figure 2:
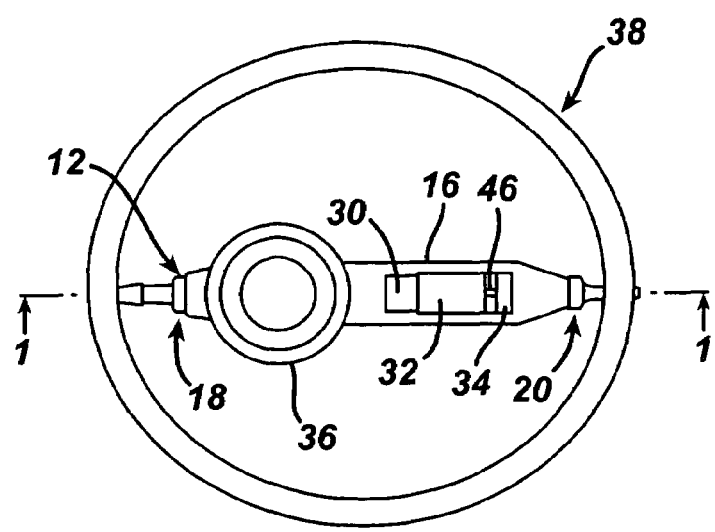
FIG. 2 is a sectional top view of the shunt valve system of FIG. 1.

Embodiments of the present invention provide an electromechanical brake mechanism that locks or secures a position of a pressure setting mechanism within a shunt valve assembly. The electromechanical brake can maintain the position of the pressure setting mechanism in the presence of a relatively strong magnetic field, such as produced by a magnetic resonance imaging device, to maintain a set pressure differential within the shunt valve assembly. Additionally, in certain cases, the shunt valve requires repositioning of the pressure setting mechanism within the shunt valve assembly to adjust a fluid flow rate through the shunt valve assembly. A clinician can activate an external controller to non-invasively release the electromagnetic brake mechanism from the pressure setting mechanism. When activated, the external controller transmits a radio frequency signal to the shunt valve assembly through magnetically coupled antennas between the controller and the shunt valve. The shunt valve assembly utilizes the signal to activate the braking mechanism and unlock the pressure setting mechanism. The clinician then operates the controller to non-invasively reposition the pressure setting mechanism and adjust the pressure at which the shunt valve opens:

FIGS. 1 and 2 illustrate an example of a shunt valve system 10 having a shunt valve assembly 12 and a controller 14. The shunt valve assembly 12 is operable to drain excess fluid from one area of a patient's body and direct the fluid to another site in the body. For example, the shunt valve assembly 12 includes a housing 16 defining an inlet port 18, an outlet port 20, and a chamber 22 oriented between the inlet port 18 and the outlet port 20. The inlet port 18 attaches to an inlet catheter 26 and the outlet port 20 attaches to a drainage catheter 28. In one embodiment, when the shunt valve assembly 12 is used to treat hydrocephalus, the inlet catheter 26 inserts within a ventricle of a patient's brain and the drainage catheter 28 inserts within another area of the patient's body, such as the right atrium of the heart or the peritoneum. During operation, the shunt valve assembly 12 carries cerebrospinal fluid (CSF), originating from the ventricle, from the inlet catheter 26, through the chamber 22, and to the drainage catheter 28.

The shunt valve assembly 12 includes a valve 30 having a pressure setting mechanism 32. The valve 30 of the shunt valve assembly 12, for example, controls the flow of excess CSF from the ventricle of a brain to another area of a patient's body. The pressure setting mechanism 32 is configured to provide non-invasive adjustment of the valve 30 within the housing 16 to adjust a pressure threshold within the shunt valve assembly 12. For example, the pressure setting mechanism 32 includes at least one magnet that allows a user to non-invasively adjust a position of the pressure setting mechanism 32. The user applies a strong external magnetic field to the shunt valve assembly 12 and rapidly switches the field to cause the pressure setting mechanism 32 to move or reposition within the housing 16. Such repositioning of the pressure setting mechanism 32 adjusts a pressure threshold at which fluid begins to flow through the shunt valve assembly 12. The pressure setting mechanism 32, therefore, ensures adequate fluid flow through the shunt valve assembly 12 and minimizes either overdrainage or underdrainage of CSF from a brain ventricle.

The shunt valve assembly 12 also includes an electromechanical brake 34, which can include an actuator, such as a solenoid, a stepper motor, or piezo motor, configured to move a brake member secure a position of the pressure setting mechanism 32 within the housing 16 and maintain the pressure threshold within the shunt valve assembly 12 at a particular level. The electromechanical brake 34, for example, has a brake member 46 that engages the pressure setting mechanism 32 to lock the relative position of the pressure setting mechanism 32 within the housing 16. The electromechanical brake 34 can effectively prevent movement of the pressure setting mechanism 32 relative to the housing 16, such as when the pressure setting mechanism 32 is exposed to environmental magnetic forces.

In certain cases, for example, the shunt valve mechanism 12 can be subjected to a strong external magnetic field, such as when a patient having an implanted shunt valve mechanism 12 undergoes an magnetic resonance imaging (MRI) procedure. The magnetic field generates a force on the magnetic pressure setting mechanism 32 within the shunt valve assembly 12 that induces motion of the pressure setting mechanism 32 within the housing 16 and can cause the pressure setting mechanism 32 to adjust the position of the valve 30. The electromechanical brake 34, however, preferably locks the pressure setting mechanism 32 in place to limit or prevent movement of the pressure setting mechanism 32 and to maintain a set pressure threshold within the shunt valve assembly 12 when exposed to the magnetic field. Additionally, the electromagnetic forces have little or no effect on the positioning of the brake member 46 of the electromechanical brake 34. The electromechanical brake 34, therefore, preferably maintains the relative position of the pressure setting mechanism 32 within the shunt valve assembly 12, in the presence of the strong electromagnetic field, to maintain the set pressure threshold within the shunt valve assembly 12.

After the shunt valve assembly 12 has been implanted within a patient 44, the valve 30 can require periodic adjustment to ensure proper flow of fluid from a source (e.g., the patient's brain ventricle) to a destination (e.g., the patient's heart). For example, when the shunt valve assembly 12 is implanted within a body 44 of a patient, the shunt valve mechanism 12 is configured with a preset fluid pressure threshold (e.g., a preset position of the valve 30 and the pressure setting mechanism 32 within the housing 16). The brake member 46 of the electromechanical brake 34 locks the position of the pressure setting mechanism 32 within the shunt valve apparatus 12 to maintain the preset fluid pressure threshold. The controller 14 operates in conjunction with the shunt valve assembly 12 to non-invasively manipulate the electromechanical brake 34 and the relative positioning of the valve 30 within the housing 16 to adjust the pressure threshold within the shunt valve assembly 12 (e.g., to adjust a fluid pressure differential between the inlet port 18 and the outlet port 20).

As illustrated in FIGS. 1 and 2, the controller 14 includes a signal transmitter 38 and the shunt valve assembly 12 includes a signal receiver 36 electrically coupled to the electromechanical brake assembly 34. Signals sent by the transmitter 38 to the receiver 36 allow for non-invasive control of the electromechanical brake assembly 34. Additionally, the controller 14 includes a valve adjustment mechanism 40, such as a magnetic element, configured to non-invasively operate the pressure setting mechanism 32 of the shunt valve assembly 12 to adjust the fluid pressure threshold within the shunt valve assembly 12.

During operation, for example, a user positions the controller 14 in proximity to the body 44, such as at a site 45 containing the shunt valve assembly 12, to electromagnetically couple the signal transmitter 38 with the signal receiver 36. The user then activates the controller 14 to transmit an activation signal, such as a radio frequency signal, from the signal transmitter 38 to the signal receiver 36. The signal receiver 36 receives the activation signal and, in response to the signal, transmits a positioning signal to the electromechanical brake 32. The positioning signal causes the electromechanical brake 32 to disengage or retract the brake member 46 from the pressure setting mechanism 32, thereby unlocking the pressure setting mechanism 32.

With the brake member 46 disengaged from the pressure setting mechanism 32, the user operates the valve adjustment mechanism 40 of the controller 14 to non-invasively adjust the pressure setting mechanism 32. For example, in one arrangement, the valve adjustment mechanism 40 is formed as a magnetic element that applies a relatively strong magnetic field to the magnetic pressure setting mechanism 32. When the controller 14 rapidly switches the magnetic field generated by the valve adjustment mechanism 40, the pressure setting mechanism 32 repositions within the housing 16, to adjust the position of the valve 30 within the housing and alter the fluid pressure threshold within the shunt valve assembly 12. After the user has adjusted the pressure threshold to a particular level, the user deactivates the signal transmitter 38 to discontinue transmission of the activation signal to the signal receiver 36. In response, the signal receiver 36 ceases transmission of the positioning signal to the electromechanical brake assembly 34, thereby causing the brake member 46 to reengage the pressure setting mechanism 32. Such reengagement locks the relative positions of the pressure setting mechanism 32 and the valve 30 within the housing 16 to maintain the pressure threshold within the shunt valve assembly 12.

FIGS. 1 and 2 illustrate the electromechanical brake 34 used in conjunction with a generic valve 30 to control fluid flow within the shunt valve assembly 12. In one arrangement, the electromechanical brake 34 can be used in a Hakim or ball-in-cone shunt valve mechanism, as disclosed by U.S. Pat. No. 4,615,691, the contents of which are hereby incorporated in its entirety by reference.

Figure 3:
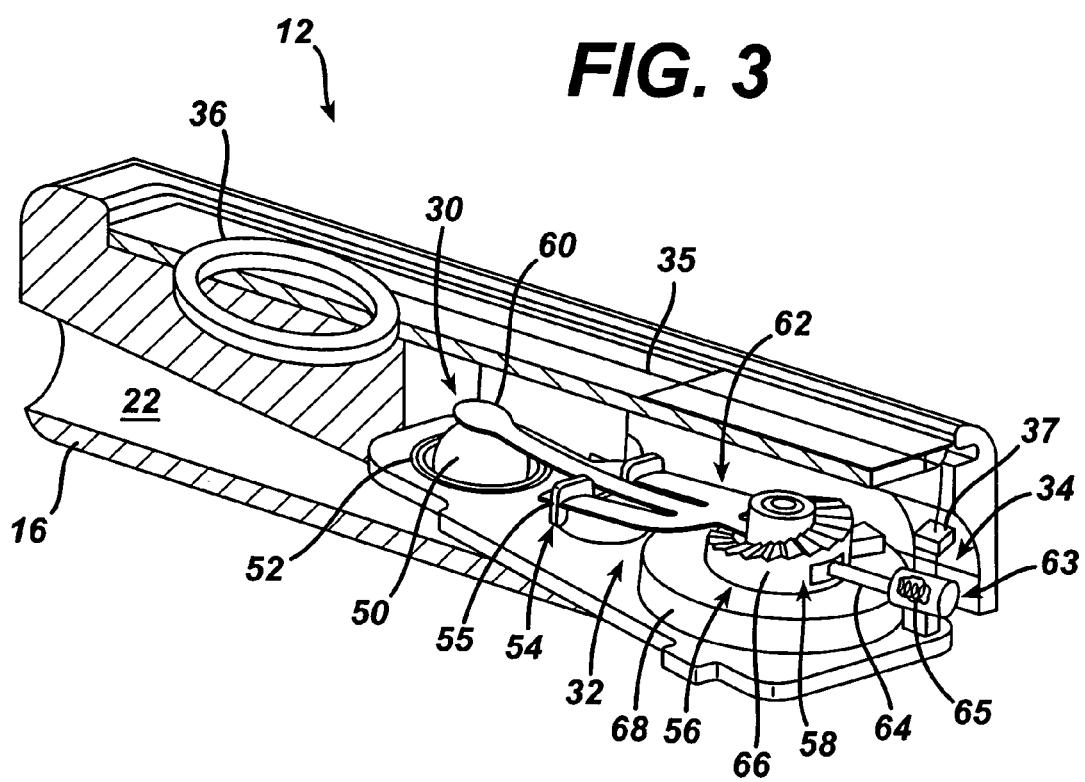
FIG. 3 is a perspective sectional view illustrating an arrangement of a shunt valve assembly of FIG. 1.

FIG. 3 illustrates the electromechanical brake 34 mounted within a Hakim shunt valve assembly 12. The Hakim shunt valve assembly 12 includes a valve 30 having a sphere 50 seated in a circular orifice 52. The Hakim shunt valve assembly 12 also includes a pressure setting mechanism 32 having a spring 54, coupled to a cantilever 55, and a rotor assembly 56. The sphere 50 regulates the pressure threshold at which fluid begins to flow through the shunt valve apparatus 12. The sphere 50 is operatively joined to a first end 60 of the cantilevered spring 54 while a second end 62 of the spring 54 engages a stair array 58 of the rotor assembly 56. Generally, the rotor assembly 56 includes the stair-step array 58 in the form of a spiral staircase. The stair array 58 of the rotor assembly 56 can be smooth or can include friction-increasing surface features (not shown). The stair array 58 can include virtually any surface feature that can increase the friction of the stair array 58. By way of non-limiting example, suitable friction-increasing surface features include grooves, detents, ridges, corrugations, roughened surfaces and combinations thereof. The rotor assembly 56 also includes at least one magnet carried in a rotor housing 68. The magnet allows a clinician to non-invasively adjust the positioning of rotor assembly 56 to set the fluid pressure threshold in the shunt valve assembly 12, as will be described in detail below.

Figure 4:
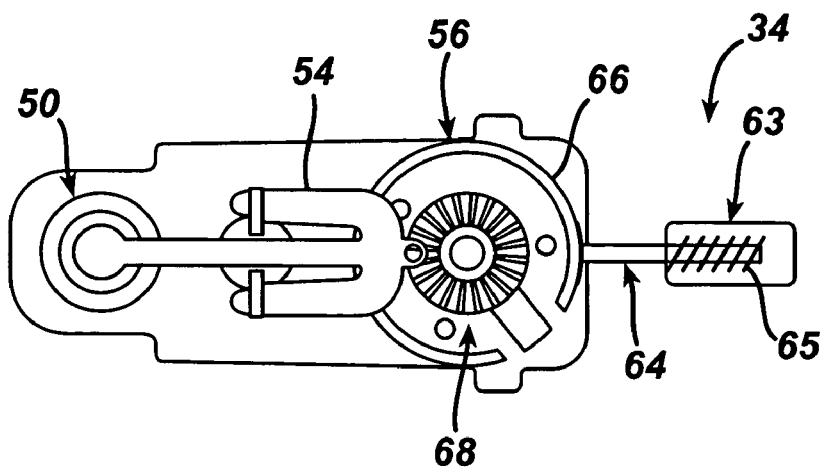
FIG. 4 illustrates a braking mechanism oriented in a released state relative to a pressure setting mechanism of the shunt valve assembly of FIG. 3.

The ball-in-cone shunt valve assembly 12 also includes an electromechanical brake 34 configured as a solenoid 63 having a magnetic brake member 64 and a spring 65 surrounding a shaft of the magnetic brake member 64. As illustrated in FIG. 4, the spring 65 biases the brake member 64 toward the rotor assembly 56 to engage a wall 66 of the rotor assembly 56 and lock the rotor 56 within the shunt valve assembly 12. In another embodiment, the brake member 64 inserts within the stair array 58 of the rotor assembly 56 to lock the relative position rotor assembly 56. Engagement of the brake member 64 with the rotor 56 effectively prevents the rotor assembly 56 from rotating within the housing 16 of the shunt valve mechanism 12, such as might be caused by external magnetic forces.

Figure 5:
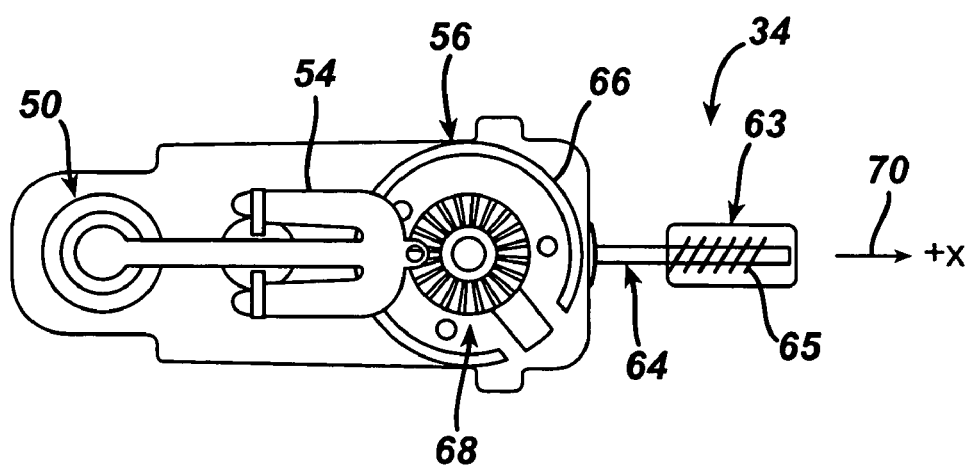
FIG. 5 illustrates a braking mechanism oriented in an engaged state relative to a rotor of the shunt valve assembly of FIG. 3.

Returning to FIG. 3, the ball-in-cone shunt valve assembly 12 can be used in conjunction with a controller 14 to allow a clinician to non-invasively adjust the pressure threshold of the shunt valve assembly 12. The shunt valve assembly 12 includes a signal receiver 36 and a signal processor 37 in electrical communication with the solenoid 63 via coupling device 35. During operation, the clinician positions the controller 14 in proximity to the ball-in-cone shunt valve assembly 12 to electromagnetically couple the signal transmitter 38 of the controller 14 with the signal receiver 36. The clinician activates the controller 14 to transmit an activation signal, such as a radio frequency signal, from the signal transmitter 38 to the signal receiver 36. The signal receiver 36 receives the activation signal and, in response to the activation signal, causes the signal processor 37 to transmit a positioning signal to the electromechanical brake 34. The positioning signal causes the electromechanical brake 34 to disengage or retract the brake member 64 from the rotor assembly 56. As indicated in FIG. 5, the positioning signal causes the solenoid 63 to generate a magnetic field, relative to the brake member 64. The magnetic field, in turn, generates a force on the brake member 64, along a +X direction 70, sufficient to overcome a spring force of the spring 65 and retract the brake member 64 from the rotor assembly 56.

With the brake member 46 disengaged from the rotor assembly 56, the clinician operates the valve adjustment mechanism 40 of the controller 14 to non-invasively adjust rotor assembly 56. As indicated above, the rotor assembly 56 includes at least one magnet carried in a rotor housing 68. The valve adjustment mechanism 40 is formed as a magnetic element that applies a relatively strong magnetic field to the magnet carried in a rotor housing 68. When the controller 14 rapidly switches the magnetic field generated by the valve adjustment mechanism 40 the rotor assembly 56 rotates within the shunt valve assembly 12 to change the pressure threshold of the shunt valve assembly 12.

For example, as the rotor assembly 34 is rotated, the second end 62 of the spring 54 moves up or down each stair of the spiral stair array 58. This results in a corresponding change in the deflection of the cantilevered spring 54. The change in the angle of deflection of the spring 54 (e.g., relative to the cantilever 55), in turn, alters the force that is exerted by the spring 54 on the sphere 50. A change in the force applied by the spring 54 to the sphere 50 results in a corresponding increase or decrease of the established pressure threshold at which fluid begins to flow through the shunt valve apparatus 12.

After the clinician has adjusted the pressure threshold shunt valve assembly 12 to a particular level, the clinician deactivates the signal transmitter 38 to discontinue transmission of the activation signal to the signal receiver 36. In the absence of a positioning signal transmitted from the signal receiver 36 to the solenoid 63, the solenoid 63 to withhold a magnetic field, relative to the brake member 64. This causes the spring 65 to expand and position the brake member 64 against the rotor 56, as illustrated in FIG. 4, to lock the position of the rotor 56 and maintain the adjusted pressure threshold within the shunt valve apparatus 12.

As described above with respect to FIGS. 1 and 3, during operation, a controller 14 transmits an activation signal to the shunt valve assembly 12, via a signal transmitter 38 to control operation of the electromechanical brake 34. The shunt valve assembly 12 receives the activation signal, via the signal receiver 36 and, in response, transmits a positioning signal to the electromechanical brake 34. The positioning signal adjusts a position of a brake member 46 of the electromechanical brake 34, relative to the pressure setting mechanism 32 of the shunt valve assembly 12. For example, in the presence of the activation signal, the electromechanical brake 34 retracts the brake member 46 from the pressure setting mechanism 32. This positioning allows a user to operate the pressure setting mechanism 32 and adjust a position of the valve 30 of the shunt valve assembly 12. In one embodiment, the signal transmitter 38 of the controller 14 and the signal receiver 36 of the shunt valve assembly 12 are inductively coupled.

Figure 6:
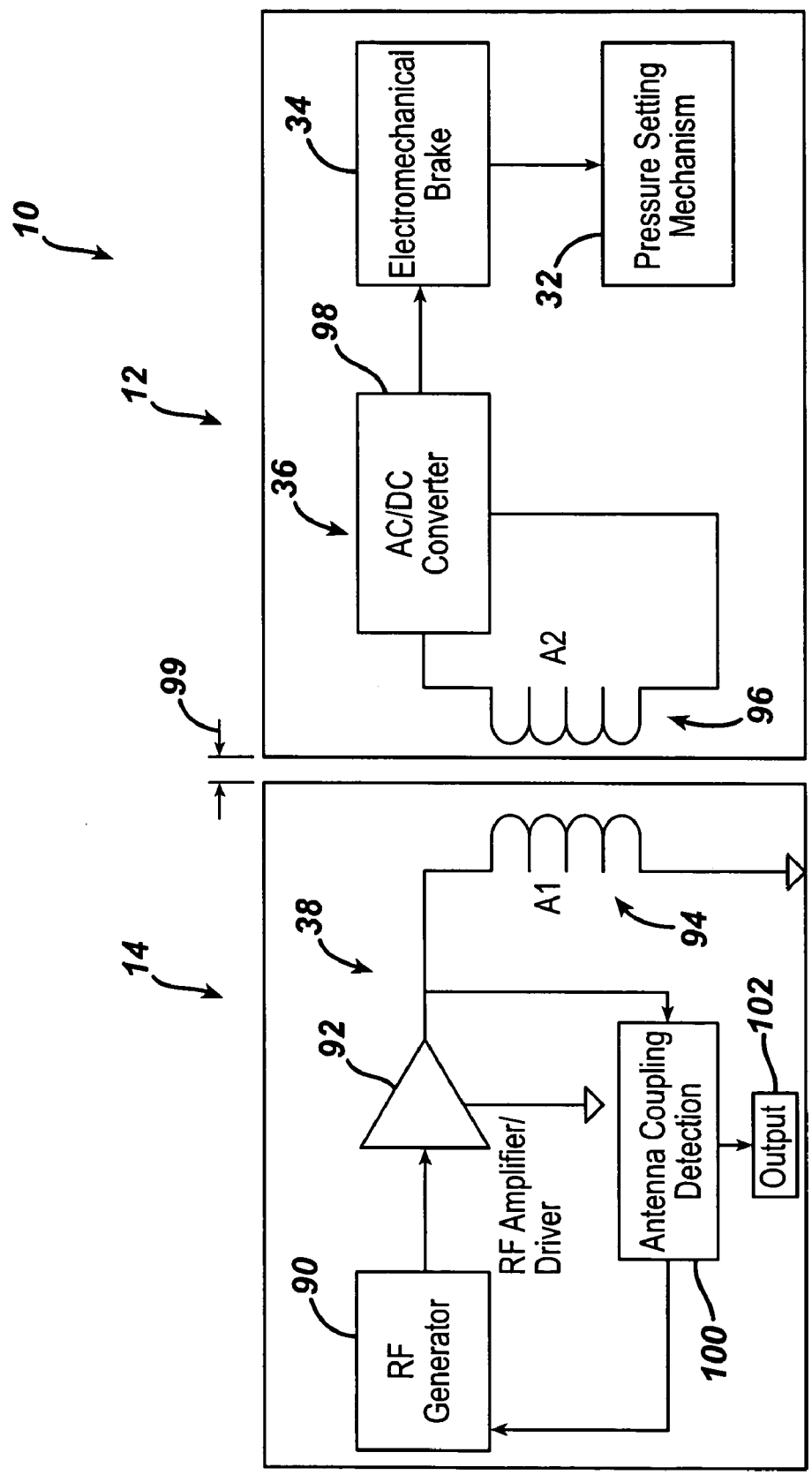
FIG. 6 illustrates a schematic representation of the shunt valve system of FIG. 1, according to one embodiment of the invention.

FIG. 6 illustrates an embodiment of the shunt valve system 10 where the controller 14 inductively couples to the shunt valve assembly 12 in order to non-invasively operate the electromechanical brake 34 of the shunt valve assembly 12. The signal transmitter 38 of the controller 14 includes a signal generator 90, a signal amplifier 92 electrically connected to the signal generator 90, and an inductive coupling mechanism 94 electrically connected to the signal amplifier 92. The signal generator 90 of the controller 14, in one arrangement, is a radio frequency signal generator. The signal generator 90 provides or generates a radio frequency signal such as a radio frequency sine wave or a pulse wave signal. The signal generator 90 provides the radio frequency signal to the signal amplifier 92. In one arrangement, the signal amplifier 92 is a radio frequency amplifier configured to amplify signals within the radio frequency range. The inductive coupling mechanism 94, for example, is an antenna formed as a wire coil having multiple windings.

Also as shown in FIG. 6, the signal receiver 36 includes an inductive coupling mechanism 96 and a signal converter 98 electrically connected to both the inductive coupling mechanism 96 and the electromechanical brake 34, such as a solenoid. The inductive coupling mechanism 96 of the shunt valve assembly 12, for example, is an antenna formed as a wire coil having multiple windings. The inductive coupling mechanism 96 is configured to inductively couple with the inductive coupling mechanism 94 of the controller 14 to receive an activation signal from the controller 14. The signal converter 98 receives the activation signal from the inductive coupling mechanism 96 and converts the activation signal to a positioning signal to operate the electromechanical brake 34, as described in detail below.

During operation, for example, a user inductively couples the controller 14 to the shunt valve assembly 12 by way of the inductive coupling mechanisms 94, 96. To affect adequate energy transfer between the inductive coupling mechanism 94 of the controller 14 with the inductive coupling mechanism 96 of the shunt valve assembly 12, the user positions the controller 14 in relatively close proximity to the shunt valve assembly 12. For example, based upon the number of windings that form the inductive coupling mechanisms 94, 96, the user can orient the inductive coupling mechanism 94 at a distance 99 between approximately 2.0 cm and 5.0 cm relative to the inductive coupling mechanism 96 of the shunt valve assembly 12. Such relative proximity of the inductive coupling mechanisms 94, 96 provides adequate inductive coupling between the controller 14 and the shunt valve assembly 12 and limits the ability for electromagnetic interference from other sources from inadvertently causing operation of the electromechanical brake 34.

As the user positions the controller 14 in proximity to the shunt valve assembly 12 the user activates the signal generator 90 of the controller 14. For example, with such activation, the signal generator 90 generates a pulse wave radio frequency signal and transmits the signal to the radio frequency amplifier 92. The signal amplifier 92 then amplifies the pulse wave signal and delivers the pulse wave signal to the inductive coupling mechanism 94. As the inductive coupling mechanisms 94 of the controller 14 carries the pulse wave signal, the inductive coupling mechanisms 94 induces a second, corresponding pulse wave signal within the inductive coupling mechanisms 96 of the shunt valve assembly 12. The inductive coupling mechanisms 96 transmits the pulse wave signal (e.g., alternating current) to the signal converter 98, which, in turn, converts the alternating current into a DC voltage to operate to the electromechanical brake 34.

As the signal converter 98 provides DC voltage to the electromechanical brake 34, the DC voltage causes the brake member 46 of the brake assembly to disengage or position away from the valve 30 of the shunt valve assembly 12. For example, in the case where the electromechanical brake 34 is a solenoid 63 having a brake member 64 (e.g., illustrated in FIGS. 4 and 5), as the solenoid 63 receives the voltage, the solenoid 63 generates a magnetic field that causes the brake member 64 to disengage from the valve 30 (e.g., disengage from the rotor 56 or pressure setting mechanism 32). Such disengagement releases the pressure setting mechanism 32 and allows the controller 14 to further adjust, non-invasively, the position of the pressure setting mechanism 32 within the shunt valve assembly 12 to adjust a fluid pressure threshold of the shunt valve assembly 12.

As described in the above example, during operation, the user positions the controller 14 in relatively close proximity to the shunt valve assembly 12 to ensure adequate inductive coupling between the controller 14 and the shunt valve assembly 12. However, in certain cases, when a user positions the controller 14 in proximity to the shunt valve assembly 12, the user might not be able to adequately determine quality or the strength of the inductive coupling between the mechanisms 94, 96. In one embodiment, the controller 14 includes an induction coupling detector 100 in electrical connection with the inductive coupling mechanism 94 of the controller 14. The induction coupling detector 100, for example, includes a controller, such as a memory and a processor, configured to measure an inductive coupling value associated with the inductive coupling mechanism 94 of the controller 14. Based on the measurement, the induction coupling detector 100 detects the quality or strength of the inductive coupling between the inductive coupling mechanisms 94, 96 and can provide a warning to a user relating to the inductive coupling strength.

During operation, in one arrangement, the induction coupling detector 100 measures an impedance value associated with the transmitter inductive coupling mechanism 94 as the inductive coupling value. For example, as the transmitter inductive coupling mechanism (e.g., transmitter) 94 induces a current in the receiver inductive coupling mechanism (e.g., receiver) 96, the receiver 96 acts as a load on the transmitter 94, thereby affecting the impedance of the transmitter 94. Once the induction coupling detector 100 measures the impedance value, the detector 100 compares the impedance value with a threshold impedance value. For example, the induction coupling detector 100 stores the threshold impedance value within a memory location associated with the detector 100. During the comparison, the detector 100 mathematically relates the measured impedance value with the threshold impedance value to form a comparison result. Based upon the comparison result, the induction coupling detector 100 generates and transmits an output signal to an output mechanism 102 associated with the controller 14 to indicate the relative strength of the inductive coupling between the transmitter 94 and the receiver 96.

The output mechanism 102 converts the output signal into an audio or visual indicator relating to the strength of the inductive coupling between the controller 14 and the shunt valve mechanism 12. In one case, assume the detector 100 generates an output signal that indicates a relatively strong inductive coupling between the controller 14 and the shunt valve mechanism 12. The output mechanism 102, in turn, can provide a user with an audio or visual indication to that indicates adequate inductive coupling of the controller 14 and the shunt valve mechanism 12. In another case, assume the detector 100 generates an output signal that indicates a relatively weak inductive coupling between the controller 14 and the shunt valve mechanism 12. The output mechanism 102, in turn, can provide a user with an audio or visual indication to that indicates inadequate inductive coupling of the controller 14 and the shunt valve mechanism 12. For example, the output mechanism 102 can provide a user with an audio or visual warning indicating that the user position the controller 14 in closer proximity to the shunt valve mechanism 12 to increase the strength of the inductive coupling between the transmitter 94 and receiver 96.

As indicated above, when the induction coupling detector 100 detects a relatively weak inductive coupling between the transmitter 94 and the receiver 96, the inductive coupling detector 100 generates an output signal that warns the user of the relatively weak inductive coupling between the transmitter 94 and the receiver 96. The warning signal causes the user to reposition the controller 14 relative to the shunt valve mechanism 12 to increase the inductive coupling between the transmitter 94 and receiver 96. In one embodiment, the induction coupling detector 100 operates to electrically adjust the impedance of the transmitter 94 to increase the inductive coupling strength between the transmitter 94 and the receiver 96 without requiring the user to reposition the controller 14 relative to the shunt valve assembly 12.

For example, the signal generator 90 has a feedback loop with the induction coupling detector 100 and the transmitter 94. The induction coupling detector 100 controls the amount of power generated by the generator 90 upon a comparison between the detected impedance of the transmitter 94 and a threshold impedance value. Such control affects a strength of the pulse wave signal produced by the signal generator 90 that, in turn, adjusts an amount of energy or power transmitted through the inductive coupling between the transmitter 94 and the receiver 96.

For example, assume the induction coupling detector 100 detects a fairly weak inductive coupling between the transmitter 94 and the receiver 96. In response to such detection, the inductive coupling detector 100 sends a signal to the signal generator 90 causing an increase of the power transmitted from the inductively coupled transmitter 94 to receiver 96. During operation, the induction coupling detector 100 continuously measures the impedance of the transmitter 94 and adjusts the output of the generator 90 to the known appropriate value stored in a memory of the induction coupling detector 100.

As indicated above, the use of the electromechanical brake assembly 34 within the shunt valve assembly 12 locks a position of a pressure setting mechanism 32 to minimize inadvertent repositioning of the pressure setting mechanism 32 or the valve 30 in the presence of strong external magnetic fields. The electromechanical brake assembly 34, therefore, can minimize either overdrainage or underdrainage of CSF from a brain ventricle. The shunt valve, however, can include additional safety feature to minimize or prevent inadvertent release of the brake member 46 of the electromechanical brake 34 relative to the pressure setting mechanism 32.

Figure 7:
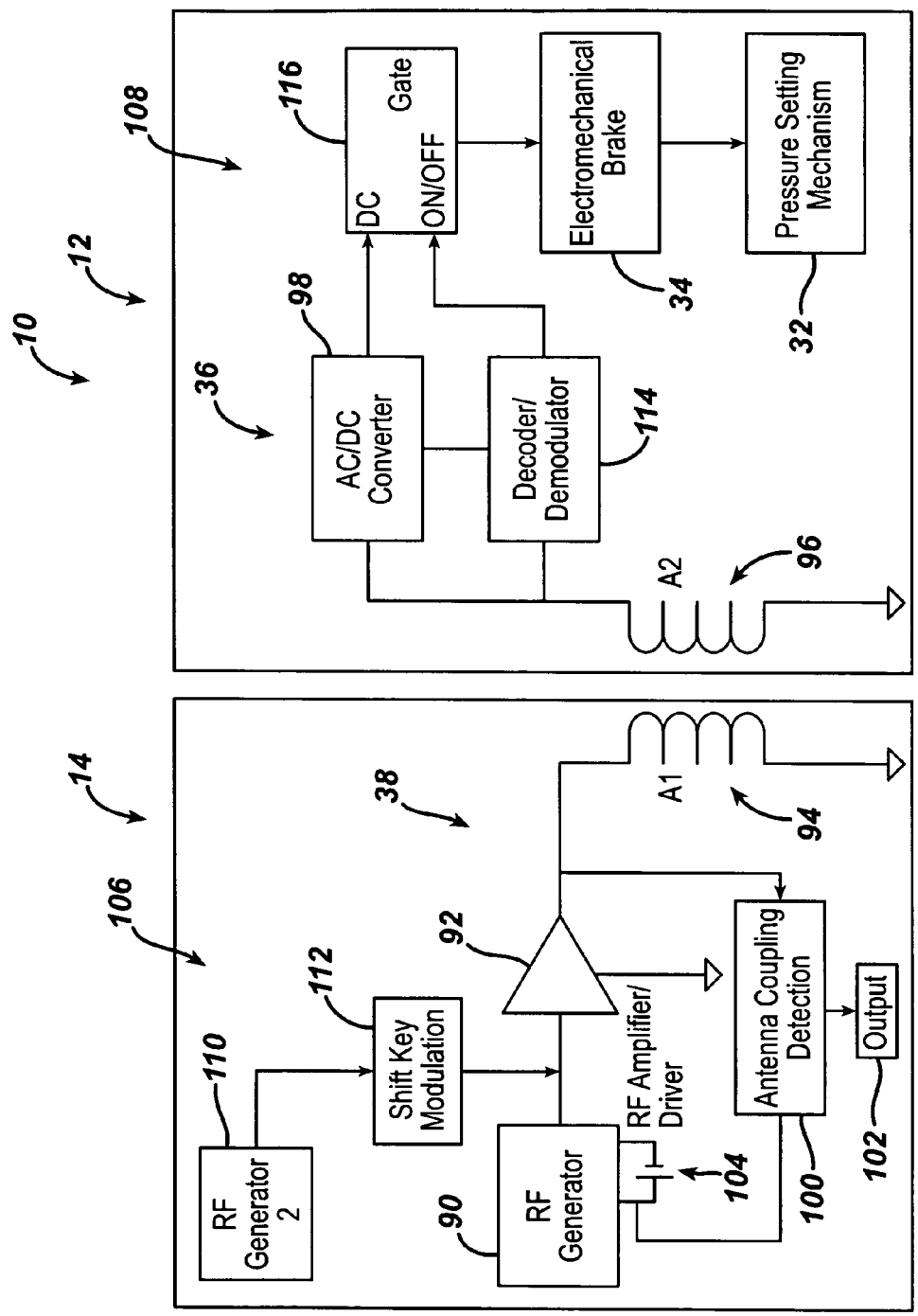
FIG. 7 illustrates a schematic representation of the shunt valve system of FIG. 1, according to one embodiment of the invention.

FIG. 7 illustrates an embodiment of the shunt valve system 10 where the shunt valve assembly 12 includes an activation signal coder 106 and an activation signal decoder 108 that minimizes or prevents inadvertent release of the brake member 46 of the electromechanical brake 34. The activation signal coder 106 of the controller 14 includes a second signal generator 110 and a shift key modulator 112 electrically connected to the second signal generator 110. The second signal generator 110, for example, is a radio frequency signal generator configured to generate a pulse wave or sine wave signal. The shift key modulator 112 receives the pulse wave from the second signal generator 10 and converts the pulse wave signal to a shift key coded signal. The activation signal decoder 108 of the shunt valve assembly 112 includes a signal decoder 114 electrically connected to a signal gate 116. The signal decoder 114 is configured to receive the coded signal from the receiver 96 and decode the coded signal into a latch signal (e.g., an on/off signal). The signal gate 116 is configured to receive the latch signal from the signal decoder 114 and, based upon the latch signal, either allow or prevent operation of the electromechanical brake 34.

For example, during operation, the first signal generator 90 generates a sine wave signal and delivers the sine wave signal, as an activation signal, to the signal amplifier 92. Additionally, the second signal generator 110 generates a sine wave signal and delivers the signal to the modulator 112. The modulator 112 encodes the signal by converting the signal to an amplitude or phase shift key modulated sine wave signal having a particular coded pattern (e.g., a pattern of 0's and 1's). The modulator 112 also transmits the encoded signal to the signal amplifier 92.

The signal amplifier 92 delivers both the activation signal, from the first signal generator 90, and the encoded signal, from the signal modulator 112, to the transmitter 94. The transmitter 94, in turn, transmits both signals to the receiver 96, via inductive coupling between the transmitter 94 and the receiver 96. The receiver 96 transfers the activation signal to the signal converter 98 and transfers the coded signal to the signal decoder 114. As the signal converter 98 receives the activation signal (e.g., an alternating current) the signal converter 90 converts the activation signal into a DC voltage signal and transmits the DC voltage signal to the gate 116. Also, as the decoder receives the decoded signal, the decoder converts the encoded signal into a latch signal (e.g., an on/off signal) and transmits the latch signal to the gate 116. Based upon the latch signal, the gate 116 either allows or disallows passage of the DC voltage signal to the electromechanical brake 94. For example, in the case where the signal decoder generates an "on" signal based upon the encoded signal, the gate 116 allows the DC voltage signal to pass to and operate the electromechanical brake. In the case where the signal decoder generates an "off" signal based upon the encoded signal, the gate 116 does not allow the DC voltage signal to pass to the electromechanical brake 34.

The use of the coded signal provides an additional safety feature to the shunt valve system 10. For example, in certain cases an external magnetic or electrical field can generate a voltage within the shunt valve mechanism 12 that could potentially cause inadvertent activation of the electromechanical brake 34. However, in the absence of a latch signal generated from a corresponding coded signal, the gate 116 of the shunt valve assembly of FIG. 7 does not allow the voltage to pass to the electromechanical brake 34. The use of the coded signal with the shunt valve system 10, therefore, minimizes or prevents inadvertent activation of the electromechanical brake 34 and maintains a fluid pressure threshold within the shunt valve mechanism 12.

While this invention has been particularly shown and described with references to preferred embodiments thereof, it will be understood by those skilled in the art that various changes in form and details may be made therein without departing from the spirit and scope of the invention as defined by the appended claims.

For example, as described above with respect to FIG. 7, the transmitter transmits two separate signals to the receiver: an activation signal and a coded signal. Such description is by way of example only. In another configuration, the controller includes a single signal generation electrically connected to the signal modulator 112. In such a configuration, during operation, the signal modulator encodes the activation signal. The transmitter 94, in turn, transmits a single signal, the encoded activation signal, to the shunt valve assembly 12 for decoding.

As described with respect to FIG. 6, the shunt valve assembly 12 includes a separate signal receiver 96 and a signal converter 98. The signal receiver 96 is configured to receive an activation signal from a controller 14. The signal converter 98 is configured to receive the activation signal (e.g., an alternating current) from the receiver 96 and convert the activation signal into a DC voltage signal. Such description is by way of example only. In another configuration, the signal receiver 96 and signal converter 98 form part of a single multifunction sensor or microprocessor, such as described in U.S. Provisional Application entitled "Pressure Sensing Methods and Devices", Ser. No. 60/661,758, filed on Mar. 15, 2005.

All publications and references cited herein are expressly incorporated herein by reference in their entirety.

What is claimed is:

1. A shunt valve assembly comprising:
 a housing having an inlet port and an outlet port, the housing configured to carry a fluid between the inlet port and the outlet port;
 a valve coupled to the housing and in fluid communication with the inlet port and the outlet port, the valve having a pressure setting mechanism configured to adjust a pressure at which the valve will release fluid from the inlet port to the outlet port;
 an electromechanical brake assembly having a brake member disposed in proximity to the pressure setting mechanism; and
 a signal receiver in electrical communication with the electromechanical brake assembly, the signal receiver configured to receive an activation signal and transmit a positioning signal to the electromechanical brake assembly, in response to receiving the activation signal, to:
  (i) position the brake member in a first position relative to the pressure setting mechanism when the activation signal has a first value, and
  (ii) position the brake member in a second position relative to the pressure setting mechanism when the activation signal has a second value.

2. The shunt valve assembly of claim 1 wherein the signal receiver comprises an inductive coupling mechanism configured to inductively couple with an activation signal source to receive the activation signal.

3. The shunt valve assembly of claim 2 wherein:
 the signal receiver configured to receive a pulse wave signal as the activation signal via inductive coupling with the activation signal source; and
 the signal receiver comprises a converter to convert the pulse wave signal to the positioning signal, the positioning signal comprising a DC voltage signal.

4. The shunt valve assembly of claim 1 wherein the signal receiver comprises a signal decoder apparatus configured to:
 receive an encoded signal from an activation signal source;
 detect a code of the encoded signal;
 compare the code of the encoded signal with a reference value; and
 transmit the positioning signal to the electromechanical brake assembly when the code of the encoded signal corresponds with the reference value.

5. The shunt valve assembly of claim 4 wherein the encoded signal comprises an encoded activation signal and wherein the signal decoder apparatus is configured to:
 receive the encoded activation signal from an activation signal source;
 detect a code of the encoded activation signal;
 compare the code of the encoded activation signal with a reference value; and
 transmit the positioning signal to the electromechanical brake assembly when the code of the encoded activation signal corresponds with the reference value.

6. The shunt valve assembly of claim 1 wherein the signal receiver is configured to receive an activation signal and transmit a positioning signal to the electromechanical brake assembly, in response to receiving the activation signal, (i) to engage the brake member with the pressure setting mechanism to secure the pressure setting mechanism relative to the housing when the activation signal has the first value and (ii) to disengage the brake member from the pressure setting mechanism to release the pressure setting mechanism relative to the housing when the activation signal has the second value.

7. The shunt valve assembly of claim 1 wherein the electromechanical brake assembly comprises a solenoid having the brake member in magnetic communication with the solenoid, the solenoid configured to receive the positioning signal from the signal receiver.

8. A shunt valve system comprising:
 a shunt valve assembly having:
  a housing having an inlet port and an outlet port, the housing configured to carry a fluid between the inlet port and the outlet port,
  a valve coupled to the housing, the valve having a pressure setting mechanism configured to adjust a pressure of the fluid carried by the housing,
  an electromechanical brake assembly having a brake member disposed in proximity to the pressure setting mechanism, and
 a signal receiver in electrical communication with the electromechanical brake assembly; and
 a controller having a signal transmitter configured to transmit an activation signal to the signal receiver of the shunt valve assembly, the signal receiver configured to receive the activation signal and transmit a positioning signal to the electromechanical brake assembly, in response to receiving the activation signal, (i) to position the brake member in a first position relative to the pressure setting mechanism when the activation signal has a first value, and (ii) to position the brake member in a second position relative to the pressure setting mechanism when the activation signal has a second value.

9. The shunt valve system of claim 8 wherein the signal transmitter comprises a transmitter inductive coupling mechanism and the signal receiver comprises a receiver inductive coupling mechanism, the transmitter inductive coupling mechanism configured to induce the activation signal in the receiver inductive coupling mechanism.

10. The shunt valve system of claim 9 wherein the transmitter inductive coupling mechanism orients in proximity to the receiver inductive coupling mechanism to induce the activation signal in the receiver inductive coupling mechanism.

11. The shunt valve system of claim 10 wherein the transmitter inductive coupling mechanism orients between about 2.0 cm and about 5.0 cm relative to the receiver inductive coupling mechanism to induce the activation signal in the receiver inductive coupling mechanism.

12. The shunt valve system of claim 9 wherein:
 the transmitter inductive coupling mechanism is configured to receive a first pulse wave signal and induce a second pulse wave signal in the receiver inductive coupling mechanism, the second pulse wave signal corresponding to the activation signal; and
 the signal receiver comprises a converter to convert the second pulse wave signal to a DC voltage signal, the DC voltage signal corresponding to the positioning signal.

13. The shunt valve system of claim 9 wherein the controller comprises an induction coupling detector in electrical communication with the transmitter inductive coupling mechanism, the induction coupling detector configured to:
 detect an inductive coupling value associated with the transmitter inductive coupling mechanism;

compare the inductive coupling value with a threshold value; and provide an output signal indicating an induction coupling strength between the transmitter inductive coupling mechanism and the receiver inductive coupling mechanism based upon the comparison of the inductive coupling value and the threshold value.

14. The shunt valve system of claim 13 wherein:

when detecting, the induction coupling detector detects an impedance value associated with the transmitter inductive coupling mechanism;

when comparing, the induction coupling detector compares the impedance value with a threshold impedance value; and when providing, providing an output signal indicating an induction coupling strength between the transmitter inductive coupling mechanism and the receiver inductive coupling mechanism based upon the comparison of the impedance value and the threshold impedance value.

15. The shunt valve system of claim 13 wherein the controller comprises:

a signal generator in electrical communication with the induction coupling detector and in electrical communication with the transmitter inductive coupling mechanism, the signal generator, induction coupling detector, and transmitter inductive coupling mechanism forming a feedback loop, the induction coupling detector adjusting an amount of power generated by the signal generator based upon a comparison of the inductive coupling value and the threshold value.

16. The shunt valve system of claim 8 wherein:

the controller comprises a signal coder apparatus configured to produce an encoded signal; and the signal receiver comprises a signal decoder apparatus configured to:

receive the encoded signal from the controller;

detect a code of the encoded signal;

compare the code of the encoded signal with a reference value; and transmit the positioning signal to the electromechanical brake assembly when the code of the encoded signal corresponds with the reference value.

17. The shunt valve system of claim 16 wherein the encoded signal comprises an encoded activation signal and wherein the signal decoder apparatus is configured to:

receive the encoded activation signal from the controller;

detect a code of the encoded activation signal;

compare the code of the encoded activation signal with a reference value; and transmit the positioning signal to the electromechanical brake assembly when the code of the encoded activation signal corresponds with the reference value.

18. The shunt valve system of claim 8 wherein the signal receiver is configured to receive an activation signal and transmit a positioning signal to the electromechanical brake assembly, in response to receiving the activation signal, (i) to engage the brake member with the pressure setting mechanism to secure the pressure setting mechanism relative to the housing when the activation signal has the first value and (ii) to disengage the brake member from the pressure setting mechanism to release the pressure setting mechanism relative to the housing when the activation signal has the second value.

19. The shunt valve shunt valve system of claim 8 wherein the electromechanical brake assembly comprises a solenoid having the brake member in magnetic communication with the solenoid, the solenoid configured to receive the positioning signal from the signal receiver.

20. A method for positioning a pressure setting mechanism of a shunt valve assembly comprising:

orienting a controller relative to a shunt valve assembly, the controller having a signal transmitter and the shunt valve assembly having a signal receiver in electrical communication with an electromechanical brake assembly, the electromechanical brake assembly having a brake member disposed in proximity to a pressure setting mechanism of the shunt valve assembly;

transmitting, via the signal transmitter, an activation signal to the signal receiver of the shunt valve assembly; and generating, via the signal receiver, a positioning signal (i) to position the brake member of the electromechanical brake assembly in a first position relative to the pressure setting mechanism when the activation signal has a first value and (ii) to position the brake member in a second position relative to the pressure setting mechanism when the activation signal has a second value.

21. The method of claim 20 comprising inductively coupling the signal transmitter with the signal receiver.

22. The method of claim 21 comprising orienting the signal transmitter in proximity to the signal receiver to induce the activation signal in the signal receiver.

23. The method of claim 21 comprising:

detecting an inductive coupling value associated with the signal;

comparing the inductive coupling value with a threshold value; and providing an output signal indicating an induction coupling strength between the signal transmitter and the signal receiver based upon the comparison of the inductive coupling value and the threshold value.

24. The method of claim 23 wherein:

when detecting, detecting an impedance value associated with the signal transmitter;

when comparing, comparing the impedance value with a threshold impedance value; and when providing, providing an output signal indicating an induction coupling strength between the signal transmitter and the signal receiver based upon the comparison of the impedance value and the threshold impedance value.

* * * * *

UNITED STATES PATENT AND TRADEMARK OFFICE
CERTIFICATE OF CORRECTION

PATENT NO. : 7,334,594 B2
APPLICATION NO. : 11/170795
DATED : June 29, 2005
INVENTOR(S) : Lev Ludin It is certified that error appears in the above-identified patent and that said Letters Patent is hereby corrected as shown below:

At column 11, line 49, after "second signal generator", change "10" to --110--.

Signed and Sealed this

Seventeenth Day of June, 2008

JON W. DUDAS
*Director of the United States Patent and Trademark Office*

UNITED STATES PATENT AND TRADEMARK OFFICE
CERTIFICATE OF CORRECTION

PATENT NO.        : 7,334,594 B2                                      Page 1 of 1
APPLICATION NO. : 11/170795
DATED             : February 26, 2008
INVENTOR(S)       : Lev Ludin It is certified that error appears in the above-identified patent and that said Letters Patent is hereby corrected as shown below:

At column 11, line 49, after "second signal generator", change "10" to --110--.

This certificate supersedes the Certificate of Correction issued June 17, 2008.

Signed and Sealed this

Twenty-second Day of July, 2008

JON W. DUDAS
*Director of the United States Patent and Trademark Office*